United States Patent [19]
Weidenbenner

[11] Patent Number: 5,873,885
[45] Date of Patent: Feb. 23, 1999

[54] SURGICAL HANDPIECE

[75] Inventor: John Joseph Weidenbenner, Ballwin, Mo.

[73] Assignee: Storz Instrument Company, St. Louis, Mo.

[21] Appl. No.: 920,307

[22] Filed: Aug. 28, 1997

Related U.S. Application Data

[60] Provisional application No. 60/025,498 Aug. 29, 1996.

[51] Int. Cl.[6] .................................................. A61B 17/32
[52] U.S. Cl. ........................... 606/171; 606/167; 606/174
[58] Field of Search ............................... 606/1, 170, 171, 606/174, 177, 51, 52, 167

[56] References Cited

U.S. PATENT DOCUMENTS

| | | | |
|---|---|---|---|
| 3,702,948 | 11/1972 | Balamuth | 310/8 |
| 3,899,829 | 8/1975 | Storm et al. | 30/228 |
| 4,622,503 | 11/1986 | Sundblom et al. | 318/645 |
| 5,020,535 | 6/1991 | Parker et al. | 606/174 |
| 5,158,108 | 10/1992 | Semaan et al. | 137/487 |
| 5,275,607 | 1/1994 | Lo et al. | 606/169 |
| 5,411,513 | 5/1995 | Ireland et al. | 606/171 |

OTHER PUBLICATIONS

"Use Of MPC Membrane Peeler Cutter", Brochure, 1980 Grieshaber & Company.

Primary Examiner—Michael Buiz
Assistant Examiner—Julian W. Woo
Attorney, Agent, or Firm—Grant D. Kang

[57] ABSTRACT

A system for controlling a plurality of ophthalmic microsurgical instruments is disclosed. Particularly, the present invention includes an ophthalmic surgical handpiece, such as an intraocular surgical scissors or forceps which is powered by an electric stepper motor. The handpiece converts the rotational motion of the stepper motor into a linear motion to operate the surgical scissors- or forceps-type instruments.

20 Claims, 3 Drawing Sheets

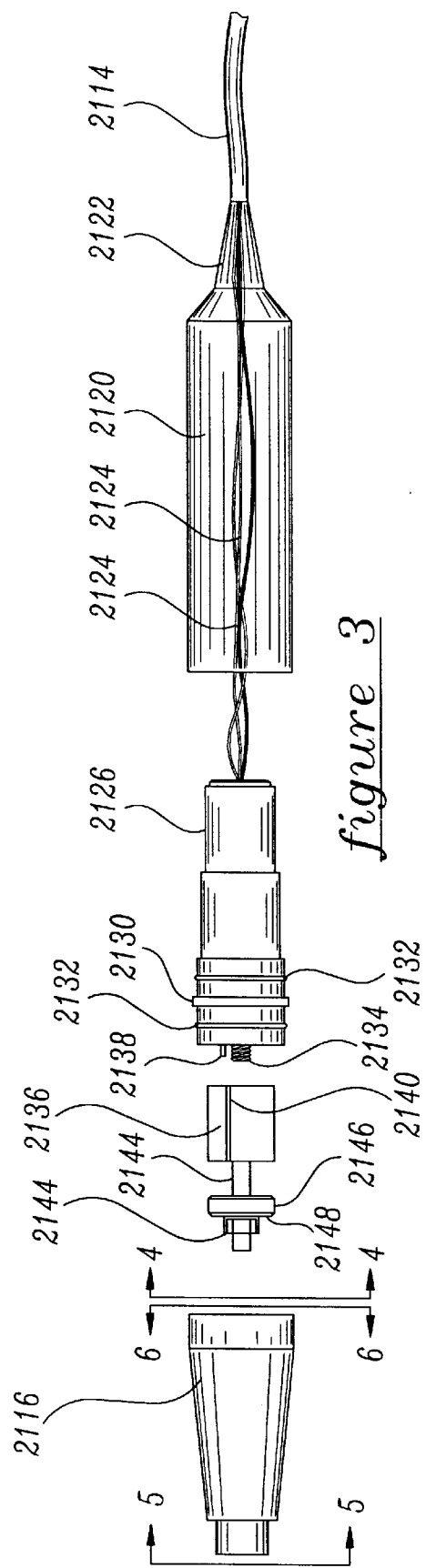
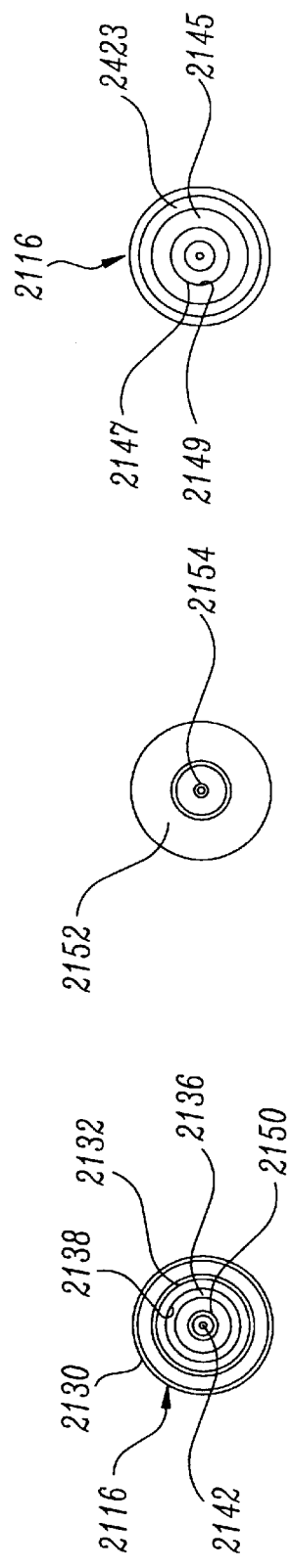
figure 3
figure 4
figure 5
figure 6

SURGICAL HANDPIECE

This application claims priority from provisional application Ser. No. 60/025,498, filed Aug. 29, 1996.

BACKGROUND OF THE INVENTION

This invention relates generally to microsurgical and ophthalmic systems and, particularly, to the field of ophthalmic surgical instruments, and more specifically, to a handpiece especially for scissors or forceps, which handpiece is actuated by a foot pedal controlled stepper motor and which provides the capability of transferring the rotary motion of the stepper motor output to linear motion, to thereby operate the surgical instrument.

Present day ophthalmic microsurgical systems provide one or more surgical instruments connected to a control console. The instruments are often electrically or pneumatically operated and the control console provides electrical or fluid pressure control signals for operating the instruments. The control console usually includes several different types of human actuable controllers for generating the control signals supplied to the surgical instruments. Often, the surgeon uses a foot pedal controller to remotely control the surgical instruments.

The use of intraocular surgical scissors is well known. While manually operated scissors are still in widespread use worldwide, they suffer from the disadvantage of being subject to human limitations on speed and accuracy. The use of surgical scissors with electric motor drive is also widespread. Electrical motor driven scissors are divided into two well known types based upon the type of drive, those that are solenoid actuated and those that are driven by a direct current motor or "proportional" control.

Most intraocular scissors have design similarities in which a pair of cutting blades extend from the end of a tubular needle with one blade being fixed and the other, opposed blade end being reciprocated between an open and a closed position with respect to the fixed blade. This reciprocating motion is accomplished through the action of one of the driving systems mentioned, such as, for example, a manual or electric motor drive.

Electric motor drivers of either rotary or linear solenoid type activate scissor closure by controlled transfer of the motor energy to the movable blade. The scissors may be of the vertical design (the guillotine, or the parallel blade type), the angled or horizontal-style, or of another design, or the driver may instead be used to actuate other instruments, besides scissors, that operate similarly (i.e., forceps).

The linear solenoid type of drive provides a reciprocating action in which the electrical actuation of a solenoid causes the movable blade to move to the closed position in relation to the fixed blade and then, usually through the operation of a spring, to return to the open position. An example of a handpiece of this type is seen in the patent which issued to Lo et al., U.S. Pat. No. 5,275,607.

One known example of a proportional control is seen in U.S. Pat. No. 4,757,814, which issued to Wang et al., for a proportional control for a pneumatic cutting device. However, that device, although disclosed as proportional, includes a linear solenoid valve actuated by a selectively varied electrical signal generated by a power supply and is controlled by a potentiometer which is in turn operated by a foot pedal.

The rotary electric motor drive may also be considered as a "proportional-cut" mode of operation because the motor is typically a stepper or rotary motor. The motion of the movable blade is controlled by the surgeon and the rate and amount of closure of the blade is proportional to the rate and amount of movement of the control device by the surgeon.

SUMMARY OF THE INVENTION

The proportional handpiece described herein provides precise control of hand instruments such as retinal scissors and retinal forceps using a rotary motor drive, rather than a linear solenoid. Moreover, the new proportional handpiece can also be used for actuating other devices, for example, it is useful for actuating an instrument for inserting, positioning, and releasing (unfolding) a foldable intraocular lens prosthesis during implantation thereof. Other convenient uses of the new device for surgical procedures requiring very fine control are certainly also conceivable. These procedures may extend to surgical areas other than ophthalmics.

The proportional handpiece of the present invention is powered by a stepper motor of known variety. The stepper motor, through a conventional gear box, provides rotating motion of a shaft. A lead screw fixed to the shaft has a driven nut attached, which nut is keyed to the handpiece housing to prevent rotation of the nut relative to the shaft. The rotating or oscillating motion of the lead screw causes the nut to move in a linear fashion. This linear motion provides the actuation necessary for the surgical instrument by striking the internally directed tip of the instrument shaft.

The stepper motor actuation, number of steps and direction of shaft movement are all controlled by a foot operated proportional switch, such as, for example, that described elsewhere herein.

The position of the jaws of the surgical instrument is relative to the position of the foot control. Thus, pressing on the foot control pedal will advance the lead screw and nut in a proportional manner. Holding the pedal in a particular position will hold the instrument jaws in a corresponding particular position. The foot pedal operated by the surgeon is in turn connected to and controlled by the modular system referred to generally as system 1.

The detection apparatus for detecting whether the presently disclosed handpiece, or some other such handpiece is connected to and controlled by the modular control system is described as the master system and is disclosed in copending U.S. application Ser. No. 08/916,851 filed Aug. 22, 1997, which application is assigned to the same company as the present application and is hereby incorporated by reference.

Thus, it is among the goals of the present invention to provide an electrically powered handpiece for surgical instruments, which handpiece is relatively easily assembled and economical to manufacture, yet still capable of being controlled by a foot actuated pedal, or other suitable control mechanisms.

It is also among the goals of the present invention, having the features enumerated, that the new handpiece include structure for transferring rotary motion to linear motion and to thereby provide the ability to the surgeon to very precisely control the movement of the surgical instrument in a proportional fashion.

Accordingly, in furtherance of the above goals, the invention includes, briefly, a proportional surgical instrument handpiece which transfers rotary motion to linear motion to thereby actuate a surgical instrument operatively connected to the handpiece. The handpiece includes a housing connectable to a surgical instrument and to a power supply. A nosepiece is attached to the housing and is operatively and detachably connectable to a surgical instrument and a proportionally operable motor is mounted within the housing and has a rotatable motor shaft which is engageable with a nut. The nut is threadably engaged with the rotatable motor shaft and has an axial shaft directed toward and contacting an end of an actuator pin of the surgical instrument when the motor is selectively operated, to thereby actuate the surgical instrument in a proportional manner. The nut is rotationally locked, so that operation of the motor and resultant rotation of the motor shaft in one direction causes the nut to move linearly within the housing, away from the motor and toward the actuator pin, and so that operation of the motor in the other direction and resultant rotation of the motor shaft in the other direction causes the nut to move linearly within the housing, toward the motor and away from the actuator pin, as the rotary motion of the motor is transferred to linear motion of the nut and nut shaft, to thereby proportionally operate the surgical instrument.

These and other goals and advantages of the invention will be in part apparent and in part pointed out hereinbelow.

BRIEF DESCRIPTION OF THE DRAWINGS

FIG. 3 is an exploded view of the handpiece of FIG. 2, with the scissors removed;

FIG. 4 is an elevation of the interior rear section of the new handpiece, taken on line 4—4 of FIG. 3;

FIG. 5 is an elevation of the front of a nosepiece of the new handpiece, taken on line 5—5, at the left side of FIG. 3; and FIG. 6 is an elevation of the nosepiece of the new handpiece, taken on line 6—6 of FIG. 3.

DETAILED DESCRIPTION OF INVENTION

Figure 1:
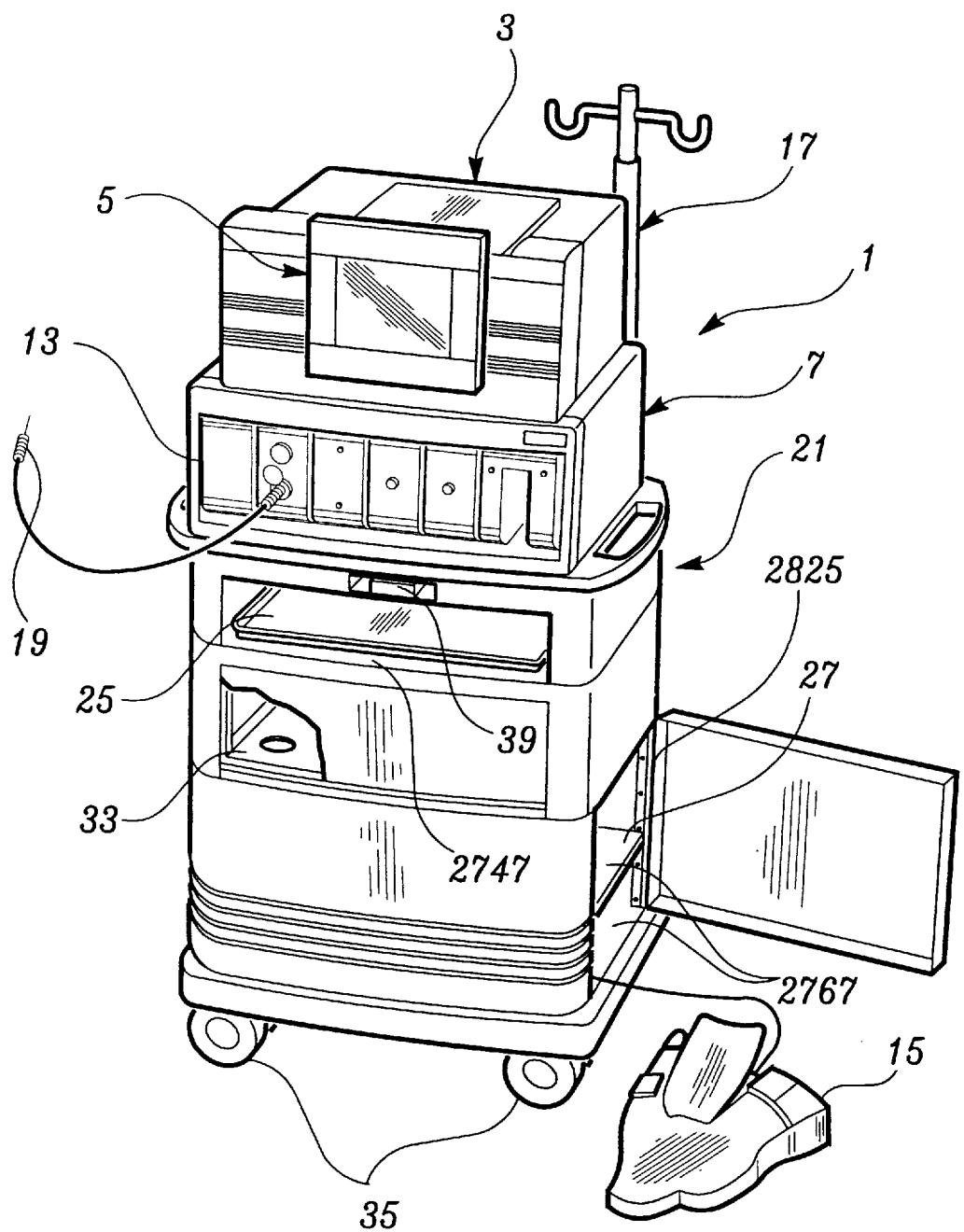
FIG. 1 is a perspective view of a microsurgical control system for use with ophthalmic microsurgical instruments and having a plurality of control modules utilizing a variety of surgical instrument or handpieces in accordance with the present invention.

Referring to the accompanying drawings in which like reference numbers indicate like elements, FIG. 1 illustrates an ophthalmic microsurgical control system 1 for use with various ophthalmic microsurgical instruments 19.

The control system 1 includes a computer unit 3 having a flat panel display 5, a base unit 7 housing a plurality of modules 13, and peripherals such as a foot control assembly 15 and a motorized intravenous (IV) pole assembly 17. Each of the modules 13 housed in the base unit 7 controls at least one ophthalmic microsurgical instrument 19 for use by a surgeon in performing various ophthalmic surgical procedures.

As is well known in the art, ophthalmic microsurgery involves the use of a number of different instruments 19 for performing different functions. These instruments 19 include vitrectomy cutters, phacoemulsification or phacofragmentation handpieces, electric microscissors, fiber optic illumination instruments, coagulation handpieces and other microsurgical instruments known in the art. To optimize performance of instruments 19 during surgery, their operating parameters differ according to, for example, the particular procedure being performed, the different stages of the procedure, the surgeon's personal preferences, whether the procedure is being performed in the anterior or posterior portion of the patient's eye, and so on.

As shown in FIG. 1, an instrumentation cart, generally designated 21, supports system 1. Preferably, the cart 21 includes a surgical, or Mayo, tray 25, the automated IV pole assembly 17, a storage compartment 27 for stowing the foot control assembly 15, disposable packs and other items, an opening 33 to house an expansion base unit (not shown in FIG. 1), and rotating casters 35. Base unit 7 and computer unit 3 preferably sit on top of instrumentation cart 21 as shown in FIG. 1 and the Mayo tray 25 is mounted on an articulating arm (not shown) preferably attached to the top of instrumentation cart 21, directly beneath base unit 7. Instrumentation cart 21 also holds a remote control transmitter, generally indicated 39, for use in remotely controlling system 1.

The modules 13 in base unit 7 house control circuits for the various microsurgical instruments 19 so that the system's user is able to configure system 1 for optimizing its use by the surgeon. As will be described in detail below, modules 13 include connections or ports by which one or more microsurgical instruments 19 connect to each module 13 and house the necessary control circuitry for controlling operation of the particular instrument or instruments 19 connected thereto. Thus, the user, by inserting the desired modules 13 in base unit 7, configures system 1 to meet a particular surgeon's preference, to control each of the instruments 19 needed for a particular surgical procedure, or to otherwise optimize system 1 for use by the surgeon.

Referring now to FIGS. 2–6, 2110 generally designates a handpiece for operating ophthalmic surgical instruments, which handpiece 2110 includes a body or housing 2112 having connected at its base or tail end 2112 a power cord 2114 and shown with a removably connected ophthalmic scissors 2160 at its nose or forwardly directed operating end 2116. In a preferred embodiment, handpiece 2110 is also for use with a scissors module, the various modules 13 being shown in FIG. 1. The various modules' 13 operation is described more fully in copending application Ser. No. 08/721,391 filed on Sep. 26, 1996, which subject matter is hereby incorporated by reference.

Scissors 2160 are illustrated as being of the horizontal, hinged variety, for example only, and it is to be understood that other types of ophthalmic instruments, such as forceps and other types of scissors, are useful with the new handpiece 2110, as well. Although handpiece 2110 could be utilized for operation of the guillotine (vertical) variety of ophthalmic scissors, this is not foreseen as the usual use of handpiece 2110, because that type of scissor does not require the precise, proportional control offered by the new handpiece 2110.

Figure 2:
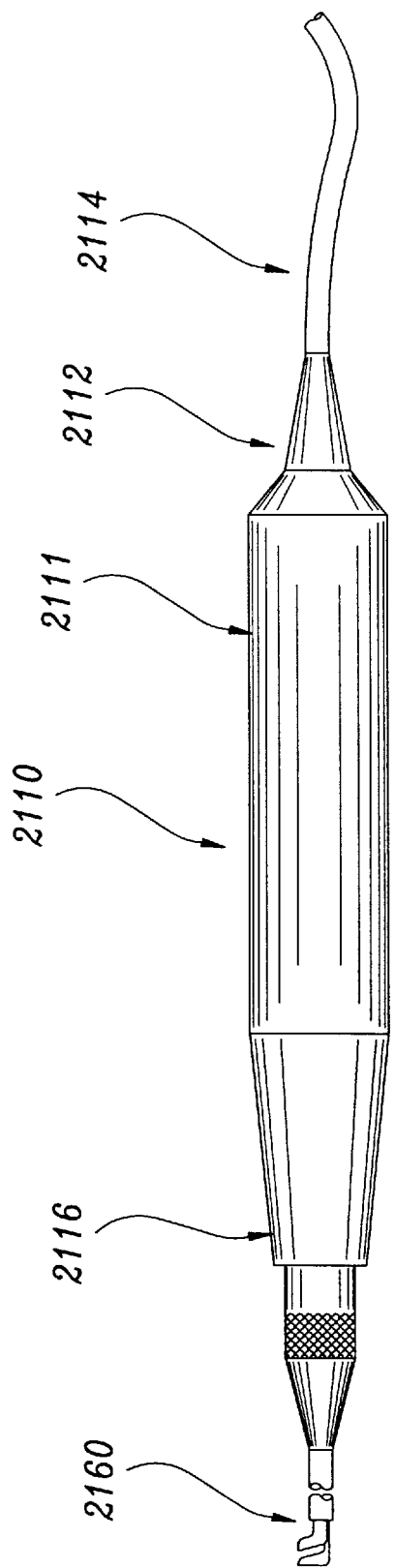
FIG. 2 is a side elevation of a handpiece for surgical instruments, constructed in accordance with the present invention, with an ophthalmic scissors attached.

FIG. 2 illustrates the external aspects of handpiece 2110, wherein scissors 2160 are shown in normal use position connected to the forwardly tapered end of a generally cone-shaped nosepiece 2116. The preferably cylindrical, rearwardly directed end of nosepiece 2116 abuts a correspondingly sized and shaped, forwardly directed end of a tubular housing 2120 which extends rearwardly toward the tail end 2112 of handpiece 2110 and is sealed there by a cable guard 2122 through which power cable 2114 passes.

Preferably, cable guard 2122 is formed of a pliable, usually synthetic substance, and is tightly connected in known manner to the otherwise open rear end of housing 2120 by having at least one O-ring (not shown) on its outer cylindrical surface for providing a tight press fit connection into housing 2120.

Clearly, the exterior of handpiece 2110 could take forms other than those shown and described and still function effectively. As examples only, the outer side wall of housing 2120 could be triangular, rectangular or oval in cross-section, rather than circular, as shown. Adjoining pieces can, in case of such an alternative, be modified in shape to connect appropriately.

Preferably, housing 2120 and nosepiece 2116 are formed of stainless steel, and, if desired for comfort of use, can have a neoprene rubber, or other coating molded or otherwise applied in an overlayer, such as is indicated in FIG. 6 at 2119. Cable guard 2122 is preferred to be formed of neoprene rubber or other suitable soft, synthetic material. However, any of the exterior portions of handpiece 2110 can be formed of other materials. For example, cable guard 2122 can be formed of aluminum or other metal. Moreover, other synthetic substances, not yet known, may be developed which are suitable for construction of some or more of the parts of device 2110.

FIGS. 3, 4 and 6 illustrate the preferred internal structure of handpiece 2110. Connected by conventional electrical wiring 2124 to power cable 2114 is an electric stepper motor 2126. Stepper motor 2126 is of a known, commercially available type having suitable specifications for performance of the functions described herein. Further, motor 2126 has a generally cylindrical shape and is longitudinally disposed, when in its operative position, within the generally central to rearward portions of housing 2120.

Although motor 2126 is preferred to be a stepper motor, for provision of proportional control of handpiece 2110, conceivably other known motors, such as DC or solenoid types, could be substituted and still at least accomplish the transfer of rotary to linear motion within handpiece 2110.

The forwardly directed end of stepper motor 2126 is fixedly connected by screws (not seen) to a cylindrical motor mount 2128 (also referred to as a bolt head) having an external ridge 2130 formed substantially centrally on the preferably cylindrical outer side wall of the motor mount for providing a secure press fit of both the motor mount 2128 and motor 2126 connected thereto within housing 2120 when handpiece 2110 is assembled for normal use.

For additional securement of the fit of the parts, O-rings 2132 or other equally effective sealing means are desirably added, for example, positioned as shown in FIG. 3, coaxially forwardly and rearwardly of ridge 2130. When handpiece 2110 is fully assembled the forwardly directed end of motor mount 2128 is coaxially disposed within the rearwardly directed end of nosepiece 2116 and the rearwardly directed end of the bolt head 2128 is coaxially disposed within the forwardly directed end of housing 2120, with the O-rings 2132 providing a snug seal between the corresponding parts. An annular seat, inside of nosepiece 2116, for the forward most O-ring 2132 on motor mount 2128 is indicated in FIG. 6 at 2123.

FIG. 3 also shows that extending longitudinally and forwardly from motor 2126, centrally through motor mount 2128 is motor shaft 2134 which is preferably a multi-pitch lead screw. Motor shaft 2134 axially engages internal threads of a nut 2136. A lock pin 2138 is fixed to and extends forwardly from the forward end of hub 2128, parallel to and radially outwardly from the position of shaft 2134.

With reference to FIGS. 3 and 4, lock pin 2138 "keys" into a correspondingly sized and shaped groove 2140 formed longitudinally in the outer side wall of nut 2136, the pin 2138 and groove 2140 being disposed in longitudinal alignment with one another when handpiece 2110 is operatively assembled.

Extending axially and forwardly from nut 2136 is a rigid shaft 2142, which is connected to nut 2136 at bushing 2144. (This element is omitted from FIG. 4, for clarity). Disposed forwardly of bushing 2144 on shaft 2142 is a press fit washer 2146, preferably formed of aluminum. Washer 2146 fits coaxially, internally of nosepiece 2116 and seats against an annular shoulder 2147, shown in FIG. 6 which is formed forwardly of a sloping internal side wall 2145 of the nosepiece, which wall 2145 extends between shoulder 2147, rearwardly to ledge 2123 which forms the gasket or O-ring 2132 seat.

Forwardly of washer 2146, which is press fit within nosepiece 2116, is a slide fit seal 2148, which is preferred to be formed of TEFLON®, or other similar moldable slick substance, and which is provided with an internal coil spring 2150 which spring 2150 biases seal 2148 radially outwardly against straight-sided retaining wall 2149 of nosepiece 2116 and inwardly against shaft 2142 as nut shaft 2142 travels longitudinally, coaxially through both seal 2148 and washer 2146 within nosepiece 2116. Wall section 2149 is indicated in FIG. 6 and extends forwardly in nosepiece 2116 until terminating in shoulder 2151. Straight-sided wall 2149 provides a cylindrical tunnel for travel therein of nut shaft 2142 coaxially through slide fit seal 2148 and press fit washer 2146.

FIG. 5 illustrates that on the forwardmost end of nosepiece 2116 there is connected by bushing 2152 a male threaded connector 2154 (see also FIG. 3) which attaches to correspondingly sized and spaced female threads on a known, commercially available surgical device, such as scissors 2160. An aperture 2143, seen in FIGS. 5 and 6, is formed in nosepiece 2116, at the forwardmost end thereof, and is in axial alignment with nut shaft 2142 when handpiece 2110 is fully assembled. Aperture 2143 axially receives the conventional actuator pin (not seen) of the scissors or other surgical instrument 19 connected by corresponding female threads to male threaded end 2154.

In use, the surgeon positions the scissors 2160 (or other appropriate instrument) within the eye, and by operation of foot control assembly 15, such as that described above and in copending application Ser. No. 08/721,391, filed Sep. 26, 1996, which is incorporated by reference herein, causes stepper motor 2126 to be activated. Such activation causes rotation of multi-pitch lead screw 2134 within locking groove 2140 on nut 2136. However, because nut 2136 is locked in its position relative to screw 2134, by virtue of pin 2138 being seated within groove 2140, nut 2136 cannot rotate with rotation of screw 2134. Rather, nut 2136 is forced to move linearly within housing 2120, either forwardly or rearwardly, depending upon the direction of rotational operation of motor 2126.

In this manner the rotational movement of the motor is converted to linear movement as the shaft 2142 of nut 2136 is slideably forced forwardly or rearwardly with the linear movement of lock nut 2136. As the forward end of shaft 2142 reaches its furthest extent of travel within nosepiece 2116 the tip of the shaft ultimately strikes and activates the rearwardly directed end of the needle of pin portion of scissors 2160, causing actuation thereof. The scissors, after cutting, or at least partially closing, depending upon the selected position of the foot pedal, will automatically return to their unactivated position due to a well known spring structure within the scissor hub 2160. The above-described structure, utilizing transfer of rotational to linear movement, is a previously unknown manner of obtaining precise, proportional control in an ophthalmic surgical instrument handpiece and responds to a long-felt need in the medical industry for improved ophthalmic surgical equipment.

In view of the foregoing, it will be seen that the several objects of the invention are achieved and other advantages are attained.

Although the foregoing includes a description of the best mode contemplated for carrying out the invention, various modifications are contemplated.

As various modifications could be made in the constructions herein described and illustrated without departing from the scope of the invention, it is intended that all matter contained in the foregoing description or shown in the accompanying drawings shall be interpreted as illustrative rather than limiting.

What is claimed is:

1. A proportional surgical instrument handpiece which transfers rotary motion to linear motion to thereby actuate a surgical instrument operatively connected to the handpiece, the handpiece comprising:

an elongated housing having a first end connectable to a surgical instrument and a second end connectable to power supply means and an outer side wall extending between the first end of the housing and the second end of the housing;

a nosepiece attached to the first end of the housing and operatively and detachably connectable to a surgical instrument;

a proportionally operable motor mounted within the housing and having a rotatable motor shaft which is engageable with a nut; and a nut threadably engaged with the rotatable motor shaft and having an axial nut shaft which is directed toward and which contacts an end of an actuator pin of the surgical instrument when the motor is selectively operated, to thereby actuate the surgical instrument in a proportional manner, the nut being rotationally locked, so that operation of the motor and resultant rotation of the motor shaft in one direction causes the nut to move linearly within the housing, away from the motor and toward the actuator pin, and so that operation of the motor in the other direction and resultant rotation of the motor shaft in the other direction causes the nut to move linearly within the housing, toward the motor and away from the actuator pin, as the rotary motion of the motor is transferred to linear motion of the nut and nut shaft, to thereby proportionally operate the surgical instrument connected to the handpiece.

2. The handpiece of claim 1, wherein the motor of the handpiece is a stepper motor.

3. The handpiece of claim 1, wherein the motor shaft is a multi-pitch lead screw.

4. The handpiece of claim 1, and further comprising a motor mount fixed to the motor and axially disposed on the motor shaft and at least partly within the housing.

5. The handpiece of claim 1, and further comprising a press fit washer axially disposed in the nosepiece.

6. The handpiece of claim 5, and further comprising a slide fit seal axially disposed on the nut shaft internally of the nosepiece, the press fit washer being coaxially disposed in the nosepiece between the nut and the slide fit seal.

7. The handpiece of claim 6, wherein the slide fit seal has an internal coil spring to thereby bias the slide fit seal radially outwardly toward an inside wall of the nosepiece and inwardly toward the nut shaft.

8. The handpiece of claim 6, wherein the press fit seal is formed of stainless steel.

9. The handpiece of claim 2, wherein the stepper motor is electrically operated.

10. The handpiece of claim 1, and further comprising a cable guard sealably connected to the second end of the housing, to thereby protect a power cable connected to the handpiece from stresses imposed upon the power cable by crimping, bending and pulling thereof.

11. The handpiece of claim 10, wherein the cable guard is press fit to the second end of the housing.

12. The handpiece of claim 10, wherein the cable guard is formed of a pliable synthetic substance.

13. The handpiece of claim 1, wherein the nut is disposed forwardly of the motor within the housing.

14. The handpiece of claim 1, wherein the nosepiece is adapted for detachable connection of a surgical instrument.

15. The handpiece of claim 1, wherein the nosepiece is formed of stainless steel.

16. The handpiece of claim 1, wherein at least part of the handpiece is provided with a soft exterior surface to thereby enhance the comfort and improve the grip of the handpiece for a user thereof.

17. The handpiece of claim 16, wherein the soft exterior surface is an exterior surface layer molded upon at least part of the handpiece.

18. The handpiece of claim 1, wherein the nosepiece is adapted for threaded engagement of the surgical instrument.

19. The handpiece of claim 4, and further comprising at least one O-ring disposed around an outer side wall of the motor mount to thereby provide a snug fit between the outer side wall of the motor mount and an inner side wall of the housing.

20. The handpiece of claim 4, wherein the motor mount is at least partly disposed within a rearwardly directed end of the nosepiece.

* * * * *